(12) United States Patent
Martenak et al.

(10) Patent No.: US 8,492,594 B2
(45) Date of Patent: Jul. 23, 2013

(54) MULTIREACTION BIFUNCTIONAL POLYMERIC CATALYST

(75) Inventors: Daniel Martenak, Perkasie, PA (US); James F. Tate, New Castle, DE (US); Jose Antonio Trejo-O'Reilly, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 111 days.

(21) Appl. No.: 13/168,137

(22) Filed: Jun. 24, 2011

(65) Prior Publication Data

US 2012/0004469 A1 Jan. 5, 2012

Related U.S. Application Data

(60) Provisional application No. 61/360,268, filed on Jun. 30, 2010.

(51) Int. Cl.
*C07C 45/73* (2006.01)
*B01J 31/10* (2006.01)

(52) U.S. Cl.
USPC ............ 568/396; 502/1; 502/2; 502/159

(58) Field of Classification Search
USPC ................. 568/396; 502/1, 2, 159
See application file for complete search history.

(56) References Cited

U.S. PATENT DOCUMENTS

| | | |
|---|---|---|
| 3,493,343 A | 2/1970 | Logan et al. |
| 3,838,043 A | 9/1974 | Crook et al. |
| 4,463,191 A | 7/1984 | D'Sidocky et al. |
| 5,096,671 A | 3/1992 | Kane et al. |
| 6,008,416 A | 12/1999 | Lawson et al. |
| 6,410,763 B1 | 6/2002 | Seidel |
| 6,977,314 B2 | 12/2005 | Vandersall et al. |
| 2003/0139629 A1 | 7/2003 | Vandersall et al. |

FOREIGN PATENT DOCUMENTS

| | | |
|---|---|---|
| CN | 1660751 A | 8/2005 |
| DE | 994137 | 6/1965 |
| DE | 1191113 | 5/1970 |
| DE | 1952481 | 4/1971 |
| DE | 1280368 | 7/1972 |
| DE | 102009011874 | 9/2010 |
| EP | 1321450 | 6/2003 |
| WO | WO0222542 | 3/2002 |
| WO | WO2009144136 | 12/2009 |

OTHER PUBLICATIONS

Sandip Talwalkar, Sanjay Mahjani; Synthesis of methyl isobutyl ketone from acetone over metal-doped ion exchange resin catayst; Applied Catalysis A: General 302 (2006) 140-148.
Willie Nicol, Elizabeth L. Du Toit; One-step methyl isobutyl ketone synthesis from acetone and hydrogen using Amberlyst CH28; Chemical Engineering and Processing 43 (2004) 1539-1545.
Elizabeth Du Toit, Renier Schwarzer, Willie Nicol; Acetone condensation on a cation exchange resin catalyst: the pseudo equilibrium phenomenon; Chemical Engineering Science 59 (2004) 5545-5550.
Nicolaas M. Prinsloo, J. Pirow Engelbrecht, Thomas N. Mashapa, Margaret J. Strauss; Acetone to MIBK process optimization through multidisciplinary chemometrics and in-line NIR spectroscopy; Applied Catalysis A: General 344 (2008) 20-29.
Claudio Burato, Paolo Centomo, Maurizio Rizzoli, Andrea Biffis, Sandro Campestrini, Benedetto Corain; Functional Resins as Hydrophilic Supports for Nanoclustered Pd(0)-Au(0) Catalysts Designed for the Direct Synthesis of Hydrogen Peroxide; Advanced Synthesis & Catalysis 2006, vol. 348, 255-259.
Hisashi Shimakoshi, Tatushi Baba, Yusuke Iseki, Ayataka Endo, Chihaya Adachi, Midori Watanabe, Yoshio Hisaeda; Photosensitizing properties of the prophycene imobilized in sol-gel derived silica coating films; Tetrahedron Letters 2008, vol. 49, 6198-6201.

*Primary Examiner* — Sikarl Witherspoon
(74) *Attorney, Agent, or Firm* — Carl P. Hemenway; Tifani M. Edwards

(57) ABSTRACT

A polymeric catalyst, and methods of using the catalyst, comprising at least one of a monosulfonated ion exchange resin, monosulfonated gel, and macroreticular resin having a particle size of less than 560 μm and metal impregnated within the resin, where the metal is palladium, platinum, iridium, rhodium, ruthenium, copper, gold, and/or silver.

9 Claims, No Drawings

MULTIREACTION BIFUNCTIONAL POLYMERIC CATALYST

This application claims the benefit of priority under 35 U.S.C. §119(e) of U.S. Provisional Patent Application No. 61/360,268 filed on Jun. 30, 2010.

This invention relates to polymeric catalysts. More particularly, this invention relates to one step multireaction bifunctional polymeric catalysts.

Catalysts typically have larger particle sizes of 600-1100 µm and ketone yield at reaction temperatures is low. Smaller particles have been disclosed, but do not necessarily result in high yield or are limited to specific catalysts. For example, in U.S. Pat. No. 6,977,314, metal-doped polysulfonated cation exchange resin catalyst with beads having a particle size of 100 µm to 2 mm is used to make ketones at a temperature of 110-150° C.

The catalyst of the invention is made of select catalyst materials and has a uniform distribution of small particles that produces an enhanced yield and decreased formation of undesirable products at a low temperature.

In a first aspect of the invention, there is provided a polymeric catalyst comprising at least one of a monosulfonated ion exchange resin, monosulfonated gel, and macroreticular resin having a particle size of less than 560 µm and metal impregnated within the resin. The metal is palladium, platinum, iridium, rhodium, ruthenium, copper, gold, and/or silver.

In a second aspect of the invention, there is provided a use of the polymeric catalyst of the invention for a reaction selected from aldol condensation, dehydration, dimerization, reduction, oxidation, alkylation, etherification, esterification, alkylation, and hydrogenation of at least one of alkynes, alkenes, aldehydes, ketones, alcohols, nitriles, amines, and nitro groups.

In a third aspect of the invention, there is provided a method of making a ketone comprising providing a polymeric catalyst of at least one of a monosulfonated ion exchange resin, monosulfonated gel, and macroreticular resin having a particle size of less than 400 µm and metal impregnated within the resin and synthesizing a ketone to produce a yield of 5-60% and a selectivity of 90-99%. The metal is palladium, platinum, iridium, rhodium, ruthenium, copper, gold, and/or silver, and the catalyst has 0.1 to 15 percent metal based on dry weight of the catalyst.

The invention is directed to a polymeric catalyst. The catalyst comprises a monosulfonated ion exchange resin, monosulfonated gel, and/or macroreticular resin, or macroporous polymer resin, and a metal. The monosulfonated ion exchange resin is a resin that comprises a moisture hold capacity of 35-85% and 0.5-2.5 equivalents per liter. One exemplary resin is the DOWEX™ MONOSPHERE™ 545C (H) available from The Dow Chemical Company. The monosulfonated gel comprises a surface area of less than 0.1 m²/g and 1-10% by weight of a crosslinker. The macroreticular resin comprises a surface area of 1-60 m²/g and 5-25% by weight of a crosslinker and has with no more than one sulfonic group. The surface area of the gel and resins is based on the Brunauer-Emmer-Teller (BET) model.

Conventional macroreticular resins are produced from the suspension polymerization of divinylbenzene (DVB)-containing monomer mixtures in the a presence of a nonsolvent These resins represent polymers having a wide range of pore size distributions and surface areas. For example, some macroreticular resins have average particle diameters from 150 to 560 microns and containing at least 60% polyvinylaromatic monomer, by polymerizing the monomers with 50 to 300% of organic cosolvents, based on total weight of monomer. In some embodiments, the average particle diameter is less than 400 microns.

Macroreticular resins ay also be prepared by polymerizing zero to 50 percent monovinylaromatic monomer and 50 to 100 percent polyvinylaromatic monomer, in the presence of 100 to 170 percent of a porogen mixture comprising a hydrophobic porogen and a hydrophilic porogen, and 0.5 to 10 percent free radical polymerization initiator, in an aqueous suspension. All percent amounts are based on total weight of monomer; and the hydrophilic porogen is present in a weight ratio of greater than 1. 2/1 up to 3/1 relative to the hydrophobic porogen; and the hydrophilic porogen is selected from one or more (C4-C10)alkanol and the hydrophobic porogen is selected from one or more (C7-C10)aromatic hydrocarbon and (C6-C12)saturated hydrocarbon.

Examples of crosslinkers include: divinylbenzene, divinylpyridine, divinylnaphthalenes, diallyl phthalate, ethylene glycol diacrylate, ethylene glycol dimethacrylate, trimethylolpropanetrimethacrylate, divinylsulfone, polyvinyl or polyallyl ethers of glycol, of glycerol, of pentaerythritol, of diethyleneglycol, of monothio or dithio-derivatives of glycols, and of resorcinol, divinylketone, divinylsylfide, allyl acrylate, diallyl maleate, diallyl fumarate, diallyl succinate, diallyl carbonate, diallyl malonate, diallyl oxalate, diallyl adipate, diallyl sebacate, divinyl sebacate, diallyl tartrate, diallyl silicate, triallyl tricarballylate, triallyl aconitate, triallyl citrate, triallyl phosphate, N,N'-methylenediacrylamide, N,N'-methylenedimethacrylamide, N,N'-ethylenediacrylamide, trivinylbenzene, trivinylnaphthalenes, and polyvinylanthracenes.

The gel resin comprises a particle size of less than 560 µm. In one embodiment, the average particle diameter is less than 400 microns. In another embodiment, the particle size is 300-350 µm.

The macroreticular resins may be prepared from crosslinked macroporous copolymers, which are polymers or copolymers polymerized from a monomer or mixture of monomers containing at least 1 weight percent, based on the total monomer weight, of polyvinyl unsaturated monomer. The porosity is introduced into the copolymer beads by suspension-polymerization in the presence of a porogen (also known as a "phase extender" or "precipitant"), that is, a solvent for the monomer, but a non-solvent for the polymer.

A crosslinked macroporous copolymer preparation, for example, may include preparation of a continuous aqueous phase solution containing suspension aids (such as dispersants, protective colloids and buffers) followed by mixing with a monomer mixture containing 1 to 85% polyvinylaromatic monomer, free-radical initiator, and, preferably, about 0.2 to 5, more preferably, about 0.3 to 3, and most preferably, about 0.4 to 1, parts porogen (such as toluene, xylenes, ($C_4$-$C_{10}$)-alkanols, ($C_6$-$C_{12}$)-saturated hydrocarbons or polyalkylene glycols) per one part monomer. The mixture of monomers and porogen is then polymerized at an elevated temperature and the porogen is subsequently removed from the resulting polymer beads by various means, for example, toluene, xylene and ($C_4$-$C_{10}$)alcohols may be removed by distillation or solvent washing and polyalkylene glycols may be removed by water washing. The resulting macroporous copolymer is then isolated by conventional means, such as dewatering followed by drying.

Suitable polyvinylaromatic monomers that may be used in the preparation of the crosslinked copolymers include, for example, one or more monomers selected from divinylbenzene, trivinylbenzene, divinyltoluene, divinylnaphthalene and divinylxylene, and mixtures thereof; it is understood that any of the various positional isomers of each of the aforementioned crosslinkers is suitable. In a preferred embodiment, the polyvinylaromatic monomer is divinylbenzene. Preferably, the crosslinked copolymer comprises about 1 to 85%, more preferably, about 5 to 55%, and most preferably, about 10 to 25%, polyvinylaromatic monomer units.

Optionally, non-aromatic crosslinking monomers, such as ethyleneglycol diacrylate, ethyleneglycol dimethacrylate, trimethylolpropane triacrylate, trimethylolpropane trimethacrylate, diethyleneglycol divinyl ether, and trivinylcyclohexane, may be used in addition to the polyvinylaromatic crosslinker. When used, the non-aromatic crosslinking monomers preferably comprise as polymerized units, from about 0 to 10%, more preferably, about 0 to 5%, and most preferably, about 0 to 2% of the macroporous polymer, based on the total monomer weight used to form the macroporous copolymer.

Suitable monounsaturated vinylaromatic monomers that may be used in the preparation of crosslinked copolymers include, for example, styrene, α-methylstyrene, ($C_1$-$C_4$) alkyl-substituted styrenes, halo-substituted styrenes (such as dibromostyrene and tribromostyrene), vinyl naphthalene, and vinylanthracene. Preferably, the monounsaturated vinylaromatic monomer is selected from styrene, ($C_1$-$C_4$)alkyl-substituted styrenes, and mixtures thereof. Included among the suitable ($C_1$-$C_4$)alkyl-substituted styrenes are, for example, ethylvinylbenzenes, vinyltoluenes, diethylstyrenes, ethylmethylstyrenes, and dimethylstyrenes. It is understood that any of the various positional isomers of each of the aforementioned vinylaromatic monomers is suitable. Preferably, the copolymer comprises about 15 to 99%, and more preferably, about 75 to 90%, monounsaturated vinylaromatic monomer units.

Optionally, non-aromatic monounsaturated vinyl monomers, such as aliphatic unsaturated monomers, for example, vinyl chloride, acrylonitrile, (meth)acrylic acids, and alkyl (meth)acrylates, may be used in addition to the vinylaromatic monomer. When used, the non-aromatic monounsaturated vinyl monomers may comprise as polymerized units, preferably, from about 0 to 10%, more preferably, from about 0 to 5%, and most preferably, from about 0 to 2% of the macroporous copolymer, based on the total monomer weight used to form the macroporous copolymer.

Porogens useful for preparing macroporous copolymers include hydrophobic porogens, such as ($C_7$-$C_{10}$)aromatic hydrocarbons and ($C_6$-$C_{12}$)saturated hydrocarbons, and hydrophilic porogens, such as ($C_4$-$C_{10}$)alkanols and polyalkylene glycols. Suitable ($C_7$-$C_{10}$)aromatic hydrocarbons include, for example, one or more of toluene, ethylbenzene, ortho-xylene, meta-xylene and para-xylene; it is understood that any of the various positional isomers of each of the aforementioned hydrocarbons is suitable. Preferably, the aromatic hydrocarbon is toluene or xylene or a mixture of xylenes or a mixture of toluene and xylene. Suitable ($C_6$-$C_{12}$) saturated hydrocarbons include, for example, one or more of hexane, heptane and isooctane; preferably, the saturated hydrocarbon is isooctane. Suitable ($C_4$-$C_{10}$)alkanols include, for example, one or more of isobutyl alcohol, tert-amyl alcohol, n-amyl alcohol, isoamyl alcohol, methyl isobutyl carbinol (4-methyl-2-pentanol), hexanols and octanols; preferably, the alkanol is selected from one or more ($C_5$-$C_8$) alkanols, such as, methyl isobutyl carbinol and octanol.

Polymerization initiators useful in preparing copolymers include monomer-soluble initiators, such as peroxides, hydroperoxides and related initiators, for example benzoyl peroxide, tert-butyl hydroperoxide, cumene peroxide, tetralin peroxide, acetyl peroxide, caproyl peroxide, tert-butyl peroctoate (also known as tert-butylperoxy-2-ethylhexanoate), tert-amyl peroctoate, tert-butyl perbenzoate, tert-butyl diperphthalate, dicyclohexyl peroxydicarbonate, di(4-tert-butylcyclohexyl)peroxydicarbonate, and methyl ethyl ketone peroxide. Also useful are azo initiators, such as azodiisobutyronitrile, azodiisobutyramide, 2,2'-azo-bis(2,4-dimethylvaleronitrile), azo-bis(α-metlaylbutyronitrile) and dimethyl-, diethyl- or dibutyl azo-bis(methylvalerate). Preferred peroxide initiators are diacyl peroxides, such as benzoyl peroxide, and peroxyesters, such as tert-butyl peroctoate and tert-butyl perbenzoate; more preferably, the initiator is benzoyl peroxide. Use levels of peroxide initiator are, preferably, about 0.3% to 5%, more preferably, about 0.5 to 3%, and most preferably, about 0.7 to 2%, based on the total weight of vinyl monomers.

Preferably, the crosslinked copolymers are selected from divinylbenzene copolymer, styrene-divinylbenzene copolymer, divinylbenzene-ethyl vinylbenzenecopolymer and styrene-ethylvinylbenzene-divinylbenzene copolymer for use as substrates for the catalysts. These crosslinked copolymers may be functionalized with functional groups according to conventional processes for monosulfonation known to those having ordinary skill in the art.

The resin or gel is impregnated with metal. Exemplary metals include palladium (Pd), platinum (Pt), iridium (Ir), rhodium (Rh), ruthenium (Ru), copper (Cu), gold (Au), silver (Ag), and mixtures thereof. In one embodiment, the metal is palladium. The metal comprises 0.1 to 15 percent metal ion based on dry weight of the catalyst.

The resin or gel may be loaded with the desired metal ion by contacting an aqueous solution of the metal ion with the hydrogen form of the ion exchange resin in a batch or continuous reactor. The metal ion may be provided in the form a metal salt, such as, for example, chlorides, bromides, nitrates, sulphates, acetylacetonates, and acetates. The loaded ion exchange resin may be rinsed free of residual salts or acid. The amount of metal salt used is chosen such that the metal or metal ion will ultimately be present in an amount of about 0.1 to 2% loading, preferably, about 0.5 to 1.5% loading, and more preferably, about 0.8 to 1.2% loading of ion exchange resin. In a preferred embodiment, the ion exchange resin catalysts contain 0.1 to 15% metal based on the dry weight of the catalyst.

A ketone, or solvent, is synthesized to produce a yield of about 5-60% with a selectivity of about 90-99%. In one embodiment, the catalyst comprises a yield of 20-50% with a selectivity of 94-99%. Yield is based on the amount of ketone produced, and selectivity is based on the amount of ketone produced relative to the total product. The catalyst also has a polydispersity, or uniformity coefficient, of less than 1.6. The uniformity coefficient is a statistical number that describes the distribution of particle size being 1.0 a monodisperse particle size material.

Possible reactions with the catalyst, include, but are not limited to, reaction selected from aldol condensation, dehydration, dimerization, reduction, oxidation, alkylation, etherification, esterification, alkylation, and hydrogenation of at least one of alkynes, alkenes, aldehydes, ketones, alcohols, nitriles, amines, and nitro groups. In one example of making the catalyst, 1 liter of ion exchange resin in hydrogen (H) form is poured into a solution of 1-50 grains of palladium acetate in 0.5-2 liters of acidified distilled water, the palladium is allowed to absorb onto the ion exchange resin for about 1 to 4 hours, and then the solution is decanted from the resin. Alternatively, the ion exchange resin may be loaded with metal by passing an aqueous solution of the metal salt through a column of the ion exchange resin until a desired level of metal ion has been retained by the resin. This may be followed by thorough washing with water to remove residual salts and acid generated during the loading process.

In one embodiment of using the catalyst, the polymeric catalyst is in the physical form of beads contained in a vessel, the beads forming a bed of the catalyst. A feed stream of ketone reactant, or solvent, such as acetone, is brought into contact with the catalyst bed in the presence of hydrogen (as a separate feed stream) for a sufficient time and temperature for a condensation reaction of the ketone to occur. The condensed liquid stream, containing reaction products (saturated ketone adduct), byproducts (unsaturated ketone adduct), and any unreacted ketone reactant that may be present, is separated from the catalyst bed, and desired ketone adduct is recovered from the liquid stream by conventional separation means (such as distillation).

One of ordinary skill in the art will be able to choose appropriate conditions, such as (1) batch operation, for example, in which the catalyst bed is loaded with the liquid stream in the presence of hydrogen, or (2) the more preferred continuous operation, for example, where the liquid stream is fed continuously into one end of a column reactor (with hydrogen) at a rate that allows sufficient residence time in the catalyst bed for the desired reaction to occur, with the condensed liquid stream being removed continuously from the other end of the bed Similarly, the reaction equipment, the choice of upflow or downflow for the direction of passage of the reactant streams through the bed, the reaction time and temperature, the particular reactants, and the method of recovering the ketone adduct, are readily selected based upon the guidance provided herein and the knowledge available to one of ordinary skill in the art.

The temperatures and pressures inside the column reactor may be selected so that the ketone reactant is at its boiling point in the catalyst bed. Variation of temperature/pressure of the ketone reactant is used to provide the desired combination of reaction temperature and conditions such that the condensation reaction takes place in the liquid phase in the catalyst bed. Conditions may be varied to provide gas phase conditions with the catalyst bed, and the conditions may be such that the condensation reaction is conducted in the liquid phase. In a preferred embodiment, a trickle bed condition, where there is liquid and gas flowing through the catalyst bed, is used. In one embodiment, the gas is hydrogen and the equilibrium liquid/vapor is acetone. Choosing a higher pressure may provide more liquid.

The polymeric catalysts of the invention may be used in condensation reactions where the ketone reactant and hydrogen are contacted under batch reaction conditions or under continuous reaction conditions. In one embodiment, the method is a continuous process based on a catalytic distillation process with the introduction of the ketone reactant being into the bottom of a column reactor immediately above a reboiler stage; in this case, the product fraction or stream is withdrawn continuously from the reboiler portion of the distillation apparatus for further processing. Preferably, the ketone reactant to undergo the condensation reaction is fed downward through the catalyst bed and a current of hydrogen is passed through the reaction zone in the same direction. However, other variations of introducing the reactant feed streams may be used, such as co-current and countercurrent hydrogen flow, flooding processes, and gaseous-phase processes.

For continuous processes, the amount of catalyst to be used, relative to the amount of reactants, is typically related to the throughput rate of the reactions, as indicated by the LHSV (liquid hourly space velocity) or liquid flow rate of reactants relative to the volume of catalyst per unit time. High LHSV may be desirable to maximize equipment usage and generation of product; however, meeting this objective must be balanced against % conversion of raw materials and % selectivity to the desired product. If the LHSV is too low, production rate of the desired product (yield and selectivity) is diminished, and the process may not be economical. If the LHSV is too high, the catalyst activity will be insufficient to provide the desired level of conversion (the process becomes "kinetically limited"). Suitable values of LHSV will typically range from, preferably, 0.5 and 10 $h^{-1}$, more preferably, from 0.5 to 8 $h^{-1}$, and most preferably, from 0.5 to 4 $h^{-1}$.

The ketone reactant may be contacted with hydrogen in the presence of the catalyst at a temperature of 65 to 200° C. and at a pressure from 1 to 100 bar (0.1 to 10 MPa) of hydrogen. Typically, the condensation reaction is conducted at a hydrogen/ketone reactant molar ratio of at least 1:1.

In another embodiment, the process may be a batch reaction with the introduction of the ketone reactant into a reactor column at the reboiler section stage of a catalytic distillation apparatus (similar to that described above). The process may then be terminated when a desired product composition of ketone adduct is achieved in the reboiler section. Alternatively, the condensation may be carried out in a batch autoclave reactor for a specified period of time, followed by cooling and recovery of the desired amount of the ketone adduct by distillation or other conventional means.

The following examples are presented to illustrate the invention. In the examples, the following abbreviations have been used.

%-w is percent by weight.
GC is gas chromatograph.
IPA is isopropyl alcohol.
LHSV is liquid hourly space velocity.
MIBK is methyl isobutyl ketone.
MPa is megaPascal.
psi is pounds per square inch.
C is Celsius; ml is milliliter; min is minute; h is hour; mm is millimeter; and cc is cubic centimeter.

Test Methods

Yield, Conversion, and Selectivity: The product from reaction is injected in a GC chromatograph. The different reaction products were analyzed and quantified. The acetone conversion is the acetone that reacts to make products, the product yield is the amount of wanted product obtained, and the selectivity is the ratio of target product to all the products determined by GC.

Dual column GC-FID Method description:
Carrier Gas: $N_2$ from High Pressure house Nitrogen
Injector: 0.2 µl volume
Inlet: Front, Mode: split, Temperature: 250° C., Pressure: 5.4 psi (37 kPa)
Split ratio: 50.0 to 1, Split flow 73.0 ml/min; Total flow 76.6 ml/min
Gas saver: 20.0 ml/min @ 2.00 min
Columns:
Column 1: Macherei Nagel 726600. Optima Wax. 30 m×250 µm×0.25 µm
Constant Pressure, Inlet: Front, Outlet: Front
Nitrogen flow: Pressure 5.4 psi (37 kPa), Flow 0.7 ml/min, Average velocity 20 cm/s
Column 2: Varian CP9151 VF1701MS Capillary 30.0 m×250 µm×0.25 µm
Constant Pressure, Inlet: Front, Outlet: Back
Nitrogen flow: Pressure 5.4 psi (37 kPa), Flow 0.7 ml/min, Average velocity 20 cm/s
Oven:
Setpoint: 40° C.
Hold time: 5 min
Ramp 1: 5.0° C./min to 115° C.
Ramp 2: 15.0° C./min to 240° C.
Final time: 6.67 min @ 240° C.
Total run time: 35 min
Detectors:
Front FID: Heater: 250° C.
Flows: $H_2$: 30 ml/min, Air: 350 ml/min, Makeup $N_2$: 30 ml/min
Signal 1: Data rate 20 Hz, peak width 0.01 min, Start 0, End 35 min
Back FID: Heater: 250° C.

Flows: H$_2$: 30 ml/min, Air: 350 ml/min, Makeup N$_2$: 30 ml/min

Signal 2: Data rate 20 Hz, peak width 0.01 min, Start 0, End 35 min

EXAMPLE

Continuous Reactor

Resin XJT-88 is a gellular strong acid cationic resin jetted with a particle size of 320 μm and was Pd loaded and reduced. 1.5 ml of total resin (wet) was charged to the columns. The following conditions were used in the making of MIBK: hydrogen at 250 cc/min, acetone at 30 ml/hour, temperature of 100-140° C. and pressure 300 psi (2.07 MPa). The product obtained after 3 hours was collected and analyzed in GC equipment. Yield and selectivity are shown in Table 1.

TABLE 1

Yield and Selectivity

| Resin | XJT-88 | Amberlite IR120 |
|---|---|---|
| Type of Resin | Gel | Gel |
| Particle Size (um) | 320 | 750 |
| Reduction | Hydrogen | Hydrogen |
| Pd (%-w dry) | 1 | 1 |
| Pressure (MPa) | 2.7 | 2.7 |
| Temperature (° C.) | 120 | 120 |
| LHSV (h$^{-1}$) | 2 | 2 |
| MIBK (%) | 55 | 40 |
| IPA (%) | 0.1 | 0.3 |
| DIBK (%) | 1.9 | 2.3 |
| Selectivity (%) | 91 | 94 |

What is claimed is:

1. A polymeric catalyst comprising:
    at least one monosulfonated gel having a particle size of less than 560 μm; and
    metal impregnated within the resin, the metal being selected from at least one of palladium, platinum, iridium, rhodium, ruthenium, copper, gold, and silver.

2. The polymeric catalyst of claim 1 further comprising a polydispersity of no more than 1.6.

3. The polymeric catalyst of claim 1 wherein the metal comprises 0.1 to 15 percent metal ion, based on dry weight of the catalyst, distributed therein.

4. The polymeric catalyst of claim 1 wherein the metal comprises palladium.

5. The polymeric catalyst of claim 1 wherein the monosulfonated gel comprises a surface area of less than 0.1 m$^2$/g and 1-10% by weight of a crosslinker.

6. The polymeric catalyst of claim 1 wherein the at least one monosulfonated gel comprises a particle size of 300-350μm.

7. A method of making a ketone comprising:
    providing a polymeric catalyst of at least one monosulfonated gel resin having a particle size of less than 400 μm and metal impregnated within the resin, the metal being selected from at least one of palladium, platinum, iridium, rhodium, ruthenium, copper, gold, and silver, the catalyst having 0.1 to 15 percent metal based on dry weight of the catalyst;
    contacting a ketone reactant and hydrogen with said polymeric catalyst to produce a saturated ketone product at a yield of 5-60% and a selectivity of 90-99%.

8. The polymeric catalyst of claim 1, wherein said polymeric catalyst is suitable for catalyzing a process in which a ketone reactant and hydrogen are brought into contact with said polymeric catalyst to produce a saturated ketone product.

9. The polymeric catalyst of claim 1, wherein said polymeric catalyst is suitable for catalyzing a process in which acetone and hydrogen are brought into contact with said polymeric catalyst to produce methyl isobutyl ketone.

* * * * *